United States Patent [19]

Golden

[11] Patent Number: 4,616,651
[45] Date of Patent: Oct. 14, 1986

[54] SURGICAL CLIP APPLIER INSTRUMENT ADAPTER JAWS

[75] Inventor: Donald M. Golden, Cherry Hill, N.J.

[73] Assignee: Ethicon, Inc., Somerville, N.J.

[21] Appl. No.: 768,532

[22] Filed: Aug. 22, 1985

Related U.S. Application Data

[60] Division of Ser. No. 723,602, Apr. 15, 1985, Pat. No. 4,570,633, which is a continuation of Ser. No. 306,436, Sep. 28, 1981, abandoned.

[51] Int. Cl.$^4$ ............................................. A61B 17/12
[52] U.S. Cl. .................................... 128/325; 128/321
[58] Field of Search ................... 128/303 R, 321, 322, 128/325, 346, 337, 311, 326; 227/DIG. 1, 143; 72/410, 481; 81/421, 422, 423, 424, 418; 29/243.56

[56] References Cited

U.S. PATENT DOCUMENTS

| | | | |
|---|---|---|---|
| 929,868 | 8/1909 | Mueller | 81/423 |
| 2,814,222 | 11/1957 | Sanders | 81/423 |
| 3,172,133 | 3/1965 | Rizzo | 81/421 |
| 3,220,241 | 11/1965 | Miller | 81/423 |
| 3,270,745 | 9/1966 | Wood | 128/325 |
| 3,439,523 | 4/1969 | Wood | 72/410 |
| 3,503,397 | 3/1970 | Fogarty et al. | 128/322 |
| 3,503,398 | 3/1970 | Fogarty et al. | 128/322 |
| 3,631,707 | 1/1972 | Miller | 128/325 |
| 3,856,016 | 12/1974 | Davis | 72/410 |
| 3,874,578 | 4/1975 | Derr et al. | 81/421 |
| 4,026,294 | 5/1977 | Mattler | 128/346 |
| 4,294,355 | 10/1981 | Jewusiak et al. | 128/325 |
| 4,361,229 | 11/1982 | Mericle | 128/325 |
| 4,434,795 | 3/1984 | Mericle | 128/303 R |

FOREIGN PATENT DOCUMENTS

| | | | |
|---|---|---|---|
| 128942 | 3/1902 | Fed. Rep. of Germany | 81/421 |
| 515205 | 11/1920 | France | 81/423 |

Primary Examiner—Richard J. Apley
Assistant Examiner—H. Macey
Attorney, Agent, or Firm—Robert L. Minier

[57] ABSTRACT

An adapter assembly is provided for a medical instrument designed to apply a first ligating clip which has a first exterior configuration. The adapter assembly is provided with an adapter member associated with each jaw of the instrument to accommodate a second ligating clip having a second exterior configuration different than that of the first clip. Each adapter member has structure for engaging a portion of one of the jaws and structure is provided for attaching the adapter assembly to at least one of the jaws in a fixed orientation with each adapter member extending beyond the tip of the jaws. Each adapter member includes a clip applying portion having a configuration adapted to cooperate with the other adapter member to receive, hold, and apply the second clip.

3 Claims, 23 Drawing Figures

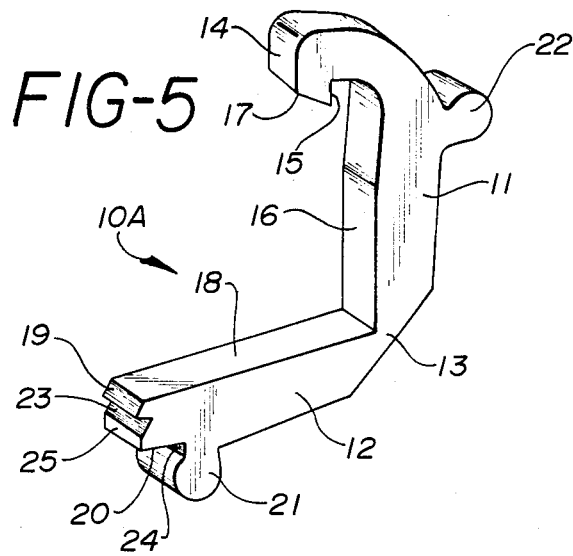
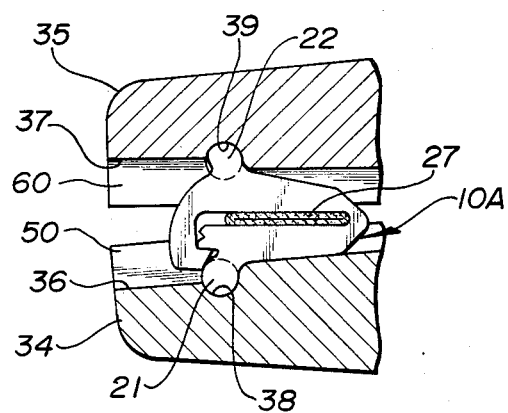
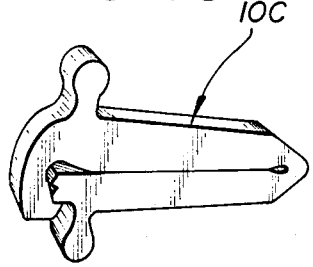
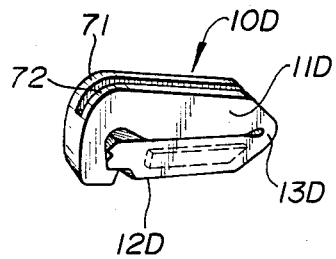
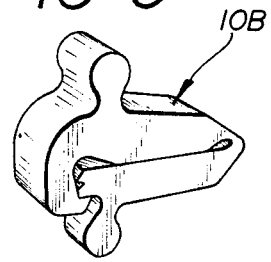
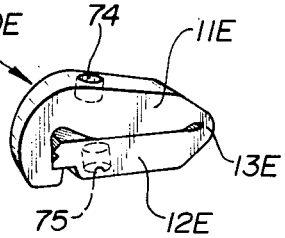

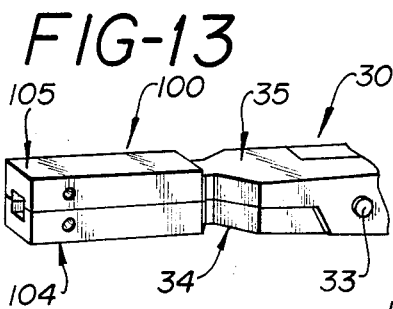
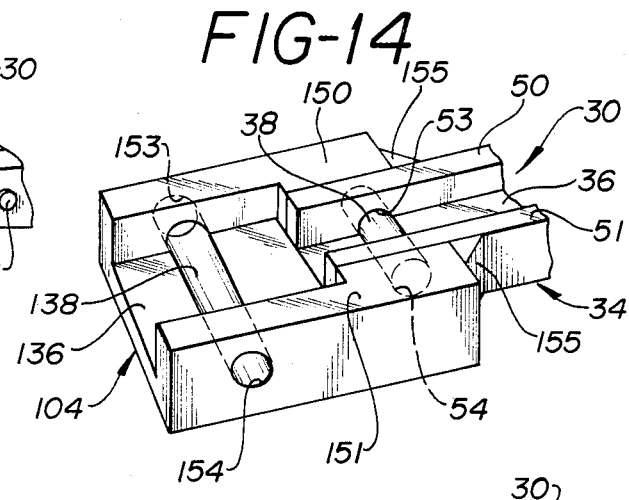
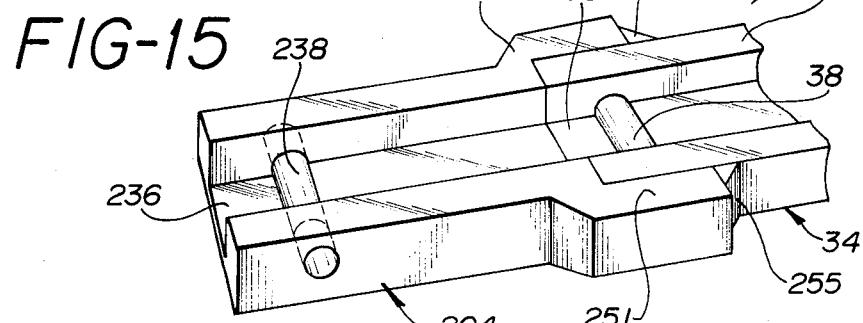
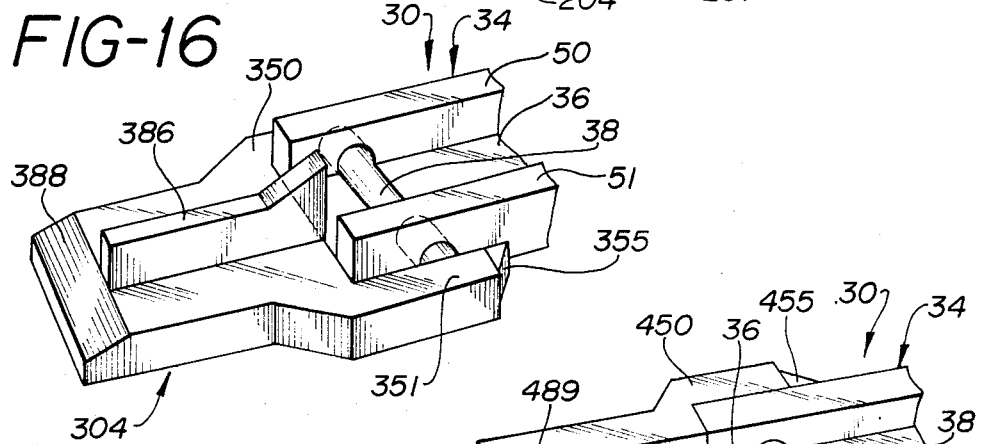
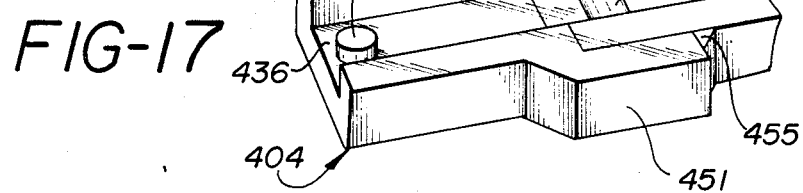

4,616,651

SURGICAL CLIP APPLIER INSTRUMENT ADAPTER JAWS

This is a division of application Ser. No. 723,602 filed April 15, 1985 now U.S. Pat. No. 4,570,633, which is a continuation patent application of patent application Ser. No. 306,436, filed Sept. 28, 1981, now abandoned.

TECHNICAL FIELD

This invention relates, in general, to an instrument for applying surgical clamps or clips, and more particularly, to an adapter jaw structure for use with such an instrument.

BACKGROUND OF THE INVENTION

Clips have been devised for clamping or strangulating various organs or vessels. For example, a clip and applicator for applying the clip to a Fallopian tube is disclosed in U.S. Pat. No. 4,169,476. A clamp and applicator for applying the clamp to a bowel is disclosed in U.S. Pat. No. 3,916,908. An example of a surgical clip applicator which incorporates a disposable cartridge is disclosed in U.S. Pat. No. 4,152,920.

Clips have been developed for use specifically in clamping or strangulating blood vessels in the human body. The clips may be fabricated from absorbable or nonabsorbable polymeric materials. Examples of such clips, and of instruments for applying such clips, are disclosed in U.S. Pat. Nos. 3,270,745; 3,326,216; 3,867,944; 3,631,707; 3,439,523; 3,439,522; 3,363,628; and 3,312,216.

In addition, various novel ligating clips are disclosed in U.S. patent applications assigned to the assignee of the present invention; Ser. No. 49,376, filed June 18, 1979, now abandoned; Ser. No. 49,379, filed June 18, 1979, now abandoned; and Ser. No. 123,878, filed Feb. 25, 1980, now abandoned. The assignee of the present invention has also developed an improved clip applier instrument specifically adapted for applying one of these types of ligating clips. The improved applier is disclosed along with the clip in the above-identified U.S. patent application Ser. No. 49,379, now abandoned. The inventor of the present invention has determined that it would be desirable to provide that improved clip applier with the capability for applying ligating clips of different designs.

SUMMARY OF THE INVENTION

A preferred embodiment of the present invention is incorporated in the medical instrument for applying a first type or kind of ligating clip. The first type of clip has an exterior configuration adapted to be engaged by the instrument.

The instrument includes two pivotally connected actuating members, each having on one end a handle and on the other end a jaw. Each instrument jaw defines a channel disposed in confronting relationship with the channel of the other jaw and extends rearwardly from the tip of the jaw for receiving, holding, and applying the first clip.

An adapter assembly is provided for the jaws to accommodate a second type or kind of ligating clip that has an exterior configuration different than that of the first clip. The adapted assembly has means for engaging or receiving a portion of each of the jaws. Means is provided for attaching the adapter assembly to the instrument in a fixed orientation extending beyond the tip of each jaw.

The adapted assembly includes two adapter members that each have a clip applying portion with a configuration adapted to cooperate with the other adapter member to receive, hold, and apply the second type of clip.

The adapter assembly thus permits a single applier instrument to be used with more than one type of clip and eliminates the need to provide a number of complete new applier instruments.

The apparatus of the present invention resides in the novel combination, construction, arrangement, and disposition of various component parts and elements incorporated in the apparatus in accordance with the principles of this invention.

The present invention will be better understood and important features other than those specifically enumerated above and will become apparent when consideration is given to the following details and description which, when taken in conjunction with the annexed drawings, describes, discloses, illustrates, and shows preferred embodiments of the present invention and what is presently considered and believed to be the best mode of practicing the principles of the invention. Other embodiments and modifications may be suggested to those having the benefit of the teachings herein, and such other embodiments and modifications are intended to be reserved, especially as they fall within the scope and spirit of the sub-joined claims.

BRIEF DESCRIPTION OF THE DRAWINGS

In the accompanying drawings forming part of the specification and in which like numerals are employed to designate like parts throughout the same.

FIG. 5 is a greatly enlarged view in perspective of a novel surgical clip for which the instrument illustrated in FIGS. 1-4 has been designed;

FIGS. 6 and 8 are views similar to FIG. 5 but showing the clip latched closed;

FIG. 7 is a view similar to FIG. 4 but showing the clip of FIGS. 5 and 6 located within the jaws of the instrument and being closed about a blood vessel;

FIGS. 9-12 are perspective views of other forms of ligating clips shown in their closed positions;

FIG. 13 is a perspective view of the front of the instrument of FIG. 1 with the instrument closed and showing one form of the adapter assembly of the present invention secured thereto;

FIG. 14 is a view similar to FIG. 13 but with the upper portion of the adapter assembly jaw omitted to better illustrate interior detail of the lower portion of the adapter assembly;

FIGS. 15, 16, and 17 are views similar to FIG. 14 but showing the lower portions of second, third, and fourth embodiments, respectively, of an adapter assembly of the present invention;

DESCRIPTION OF THE PREFERRED EMBODIMENTS

This invention may be used in many different forms. The specification and the accompanying drawings disclose specific embodiments as examples of the use of the invention. The invention is not intended to be limited to the embodiments illustrated, and the scope of the invention will be pointed out in the appended claims.

The precise shapes and sizes of the components herein described are not essential to the invention unless otherwise indicated. The particular shapes and sizes are shown to best illustrate the principles of the invention.

The choice of materials for constructing the illustrated apparatus is dependent upon the particular application involved and other variables, as those skilled in the art will appreciate. In the following description, three digit numerals in the 100 series are used to refer to the first embodiment of the adapter assembly illustrated in FIGS. 13 and 14, three digit numerals in the 200 series are used to refer to the second embodiment illustrated in FIG. 15, three digit numerals in the 300 series are used to refer to the third embodiment illustrated in FIG. 16, three digit numerals in the 400 series are used to refer to the fourth embodiment illustrated in FIG. 17, three digit numerals in the 500 series are used to refer to the fifth embodiment illustrated in FIGS. 18 and 19 and to the modification of the fifth embodiment illustrated in FIG. 20, and three digit numerals in the 600 series are used to refer to the sixth embodiment illustrated in FIGS. 21-23. The same last two digits in each numeral designates similar or functionally analogous elements in the various embodiments.

Figure 1:
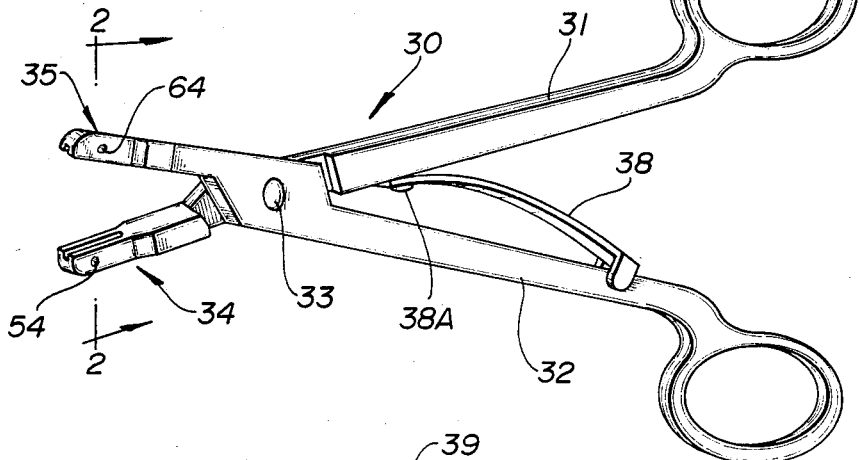
FIG. 1 is a forceps-type instrument for applying a first type of ligating clip.

In the preferred form of the invention disclosed herein, the invention is designed to be incorporated in, or made part of, a modification of the forceps-type ligating clip applier disclosed in the above-identified U.S. patent application, Ser. No. 49,379, now abandoned. The modified forceps-type ligating clip applier is illustrated in FIG. 1 in the drawings of this disclosure and is designated generally therein by reference numeral 30.

The applier 30 comprises two actuating members or handle members 31 and 32 crossing at a pin or hinge point 33 and maintained in a normally open position by a spring 38 which is secured by suitable means, such as a rivet 38A, to the handle 31. The handle 31 extends beyond the hinge point 33 to form a jaw member or jaw 34. Similarly, the handle 32 extends beyond the hinge point 33 to form a jaw member or jaw 35.

Figure 2:
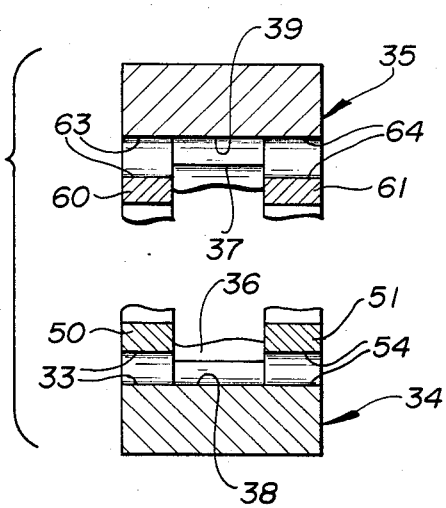
FIG. 2 is a greatly enlarged, fragmentary, cross-sectional view taken generally along the plane 2—2 in FIG. 1.
Figure 3:
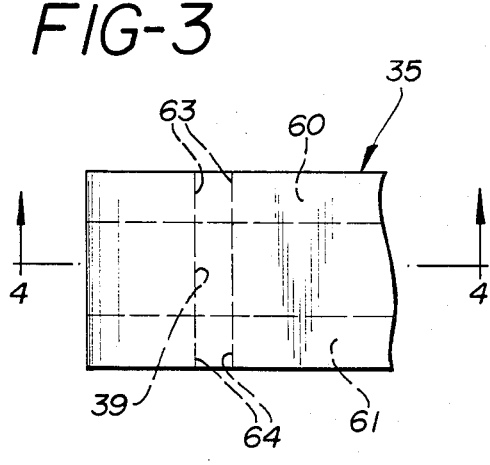
FIG. 3 is a greatly enlarged, fragmentary, top view of the upper jaw of the instrument illustrated in FIG. 1.
Figure 4:
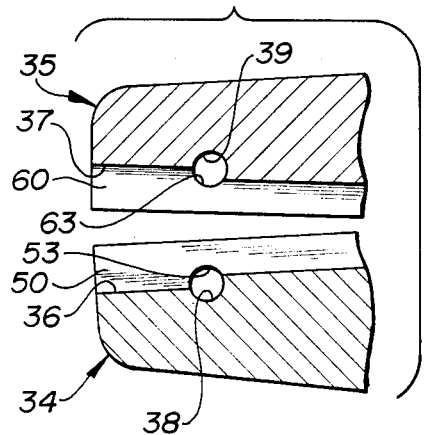
FIG. 4 is a fragmentary, cross-sectional view taken generally along the plane 4—4 in FIG. 3.

As best illustrated in FIGS. 2, 3, and 4, jaws 34 and 35 are of identical design. Jaws 34 and 35 are provided respectively with channels 36 and 37 extending rearwardly from the tips of the jaws. In the lower jaw 34, the channel 36 is defined between the two spaced-apart upwardly extending walls 50 and 51. Similarly, the upper jaw 35 has two spaced-apart downwardly extending walls 60 and 61 which define the sides of the channel 37.

The channel 37 of the upper jaw 35 is provided with a partially cylindrical recess 39 extending across the width of the channel. Similarly, the channel 36 of the lower jaw 34 is provided with a partially cylindrical recess 38 extending across the width of the channel. The recesses 38 and 39 are generally in alignment when the jaws of the instrument are closed and are sized to receive portions of a ligating clip described in detail hereinafter.

In the preferred form of the instrument 30 illustrated in FIG. 1, the instrument is fabricated from a suitable type of stainless steel and the recesses 38 and 39 are formed in the jaws 34 and 35, respectively, by drilling a hole through each jaw. As illustrated for the upper jaw 35 in FIGS. 2 and 3, this drilling produces a bore 63 in the wall 60 and a bore 64 in the wall 61. The bores 63 and 64 are coaxially aligned and are formed by a single drilling operation that also forms the partially cylindrical recess 39. Similarly, in the lower jaw 34, bores 53 and 54 are formed in the walls 50 and 51, respectively, along with the recess 38 by drilling through the jaw.

When the instrument 30 is fabricated from the stainless steel, it is preferable to form the partially cylindrical recesses 38 and 39 in the jaws of the instrument by means of drilling through the jaw walls as described above. However, the instrument 30 may be fabricated from other materials, such as from molded thermoplastic polymer compounds. With such a construction, the partially cylindrical recesses 38 and 39 may be molded directly into the jaws 34 and 35, respectively. This would eliminate any need to drill the sidewalls of the jaws to form the recesses. Consequently, jaw sidewall bores would not be present in such an instrument.

In any case, the instrument 30 functions to apply a novel ligating or hemostatic clip to close a severed blood vessel or other small fluid duct. The novel clip is illustrated in FIGS. 5 and 6 and is designated generally therein by the reference numeral 10A. In FIG. 5, the clip 10A is shown in an open position and in FIG. 6 the clip is shown in a latched closed position.

With continued reference to FIGS. 5 and 6, the clip 10A is seen to be formed with two leg segments 11 and 12 connected at the proximal ends thereof by a hinge section 13. The leg segment 11 terminates at the distal end thereof in a hook member 14 having an inner face 15 substantially parallel to an inner face 16 of the leg 11 segment and forming an acute angle with an end face 17.

The leg segment 12 terminates at the distal end in an end face 19 which forms an obtuse angle with an inner face 18 of the leg segment 12. The end face 19 is offset at 23 to form a notch approximately midway between the inner face 18 and a bottom face 20. Additionally, the leg segment 12 is squared off at a face 25 to form a substantially right angle with the bottom face 20.

The length and width of the inner faces 16 and 18 are substantially equal and the face 15 of the hook member is spaced from the inner face 16 of the leg segment 11 by a distance corresponding to the thickness of the leg segment 12 between the planes of the inner face 18 and the bottom face 20.

When the leg segments 11 and 12 are pivoted about the hinge section 13 to bring the inner faces 18 and 16 into opposition, the hook member 14 is deflected by the end face 19 of the leg segment 12 until the distal end of the leg segment 12 snaps under the hook member 14 and is thereby locked in place as best illustrated in FIG. 6. The end face 17 of the hook member 14 and the end face 19 of the leg segment 12 are angled as illustrated in FIG. 5 to facilitate the passage of the leg segment 12 past the hook member 14 during clip closure.

The surfaces of the inner faces 16 and 18 may be smooth as illustrated in FIG. 5, or may be provided with ridges or grooves to increase vessel holding power. The leg segment 11 may also be undercut at the juncture of the hook member 14 and the inner face 16 as illustrated in FIG. 5 to increase the deflectability of the hook member 14 and increase the space between the hook member 14 and the leg segment 11. This compensates for any inward deflection of the hook member 14 during closure which might reduce the clearance between the surfaces 15 and 16 and otherwise interfere with the latching of the clip.

With continued reference to FIGS. 5 and 6, the leg segment 12 of the clip 10A includes an outside cylindrical boss 21 extending across the width of the leg segment 12 near the distal end thereof. Similarly, the leg segment 11 has a boss 22 extending across the width of the leg segment 11 near the distal end thereof. The cylindrical bosses 21 and 22 are equidistant from the hinge section 13 so that when the clip 10A is closed, the bosses 21 and 22 define a line perpendicular to the major axis along the length of the clip as best illustrated in FIG. 6. The boss 21 is spaced from the face 25 a distance sufficient to permit the full engagement of the hook member 14 by the leg segment 12 when the clip 10A is in the closed and latched position.

The distal end of the leg segment 12 forward of the boss 21 is of reduced thickness relative to the thickness immediately to the rear of boss 21, thereby forming a step 24 between the boss 21 and the bottom surface 20. The significance of this clip configuration will be appreciated in connection with the description hereinafter of the application of the clip by means of the instrument 30.

The instrument 30 is used to apply one clip 10A at a time to a blood vessel or other fluid conduit. Initially, the clip 10A is loaded in the clip applier instrument 30 when the instrument 30 is in the open position as illustrated in FIGS. 1 and 4. After moving the jaws of the instrument and the clip into position over the vessel to be ligated, the jaws of the instrument are closed as illustrated in FIG. 7 and the clip is locked into position over the vessel 27. As can be seen in FIG. 7, the clip boss 22 is received in the partially cylindrical recess 39 of the instrument upper jaw 35 and the clip boss 21 is received in the partially cylindrical recess 38 of the instrument lower jaw 34.

As best illustrated in FIGS. 4 and 7, the portions of the instrument channels 36 and 37 forward of the recesses 38 and 39, respectively, are deeper than the portions of the channels behind the recesses. When the open clip is held in the instrument 30, the bosses 21 and 22 extend into the cylindrical recesses in each jaw and, due to the angle of the open clip in the open instrument 30, the distal ends of the leg segments of the clip extend into the deeper forward channel portions of the instrument jaws. The reduced thickness of the leg segment 12 of the clip at the distal tip prevents interference between the tip of the clip 10A and the channel 36 of the lower jaw 34 when the clip 10A is held in the open position.

As the instrument 30 is operated to close the clip 10A, the bosses 21 and 22 rotate in the cylindrical recesses of the jaws 34 and 35, respectively, until the outer surface of the leg segment 12 rests on the rear portion of the bottom of channel 36 as illustrated in FIG. 7. At this point, the distal end of leg segment 12 has rotated away from the face of the channel 36 and a sufficient space exists for the hook member 14 to bypass the leg segment 12 and latch over the outer surface thereof.

After the clip 10A has been securely latched over the vessel 27, the jaws 34 and 35 of the instrument 30 are opened to release the clip 10A and the vessel 27. A new clip may then be loaded into the instrument 30. Since the jaws of the applier 34 and 35 are identical, it is not necessary to orient each jaw of the instrument 30 to a specific leg of the clip when loading the instrument 30.

The clip 10A illustrated in FIGS. 5-7 can be constructed in various sizes according to its intended function. Hemostatic clips are typically less than 6 mm in length, are about 1.5 mm in width, and have a vessel clamping surface of about 3 mm in length. The dimensions of the clip may be reduced about 50% for certain applications in microsurgery. Larger clips for special hemostatic applications, or for other functions such as the closure of oviducts or vas-deferens, may have dimensions of about double those of a typical hemostatic clip. The various sizes of clips are preferably matched with individual appliers having jaws tailored to the size of the clip for the best performance.

The clips are most conventionally molded of biologically acceptable plastic materials which may be absorbable or non-absorbable. Preferred absorbable polymers include homopolymers and copolymers of glycolide and lactide, and poly(p-dioxanone). Preferred non-absorbable polymers include nylon and polypropylene. All these materials have been demonstrated to be biologically acceptable when used as sutures or other implantable medical devices. The clips may also be cast or machined from solid polymeric materials or from metals such as aluminum, magnesium, stainless steel, tantalum, and various alloys of these, some of which may also be absorbable in biological tissue.

Other types of clips have been proposed for use in clamping blood vessels and other fluid conduits in the human body. Some other clip configurations are illustrated in FIGS. 9-12 which are all drawn to the same scale for convenient reference. Also, for comparision purposes, FIG. 8 illustrates the above-discussed clip 10A of FIGS. 5 and 6 drawn to the same scale as the clips of FIGS. 9-12. These other clip designs are described next. A description of a novel adapter assembly for enabling the instrument 30 to apply the various clips follows the description of the clips.

FIG. 9 illustrates a clip 10B which is similar to the clip 10A illustrated in FIGS. 5, 6, and 8 but which is much wider. FIG. 10 illustrates a clip 10C which is similar to the clip 10A illustrated in FIGS. 5, 6, and 8 but which is much longer. The exterior configurations of clips 10B and 10C are thus different than the exterior configuration of clip 10A to the extent that the clips are of different lengths or thicknesses. However, clips 10B and 10C function in the same manner as clip 10A.

FIG. 11 illustrates a clip 10D that latches closed in a manner identical to that of the clip 10A described above with reference to FIGS. 5, 6, and 8. However, the clip 10D has an exterior configuration that is different than that of the clip 10A. Specifically, the clip 10D has a leg segment 11D connected to a leg segment 12D by means of a flexible section 13D. Leg segment 11D has a channel or recess defined between two walls or rails 71 and 72. The lower leg segment 12D has a similar configuration.

FIG. 12 illustrates a clip 10E which has an upper leg segment 11E and a lower leg segment 12E which are connected together by a flexible section 13E. The upper leg segment 11E has a cylindrical recess or bore 74 opening to the top of the clip. Similarly, the lower leg segment 13E defines a bore 75 communicating with the bottom surface of the clip.

The inventor of the present invention has determined that it would be desirable to provide means for modifying the clip applier instrument 30 (FIG. 1) to provide the instrument 30 with the capability for applying clips having an exterior configuration different than that of the clip 10A (FIGS. 5, 6, and 8). It would be desirable to provide means for enabling the instrument 30 to apply the clips illustrated in FIGS. 9–12, as well as other clips. To this end, the inventor of the present invention has invented a novel adapter assembly for cooperating with the instrument 30. The adapter assembly may be provided in a variety of forms to function with a variety of different clips and enable the instrument 30 to apply the various clips to a blood vessel or other other duct.

FIG. 13 illustrates the instrument 30 with a first embodiment of a novel adapter assembly 100 provided thereon. The adapter assembly 100 comprises a first or lower jaw adapter member 104 associated with the instrument lower jaw 34 and a second or upper jaw adapter member 105 associated with the instrument upper jaw 35. The adapter members 104 and 105 are identical. The structure of each member 104 and 105 will be described with reference to FIG. 14 which illustrates the lower adapter member 104 in detail.

The adapter member 104 is provided with means for engaging or receiving a portion of the instrument lower jaw 34. Specifically, the adapter member 104 has a pair of spaced-apart mounting walls 150 and 151 with rearwardly extending portions between which the lower instrument jaw 34 is disposed. The mounting walls 150 and 151 each have an inner surface facing toward the inner surface of the other mounting wall. At least a rear portion of the inner surface of each wall 150 and 151 of the adapter member 104 is arranged in face-to-face relationship with an exterior side surface of each associated instrument lower jaw wall 50 and 51, respectively.

The adapter member 104 is either releasably or permanently secured to the instrument 30 by attaching each of the spaced-apart walls 150 and 151 to the sides of the lower jaw 34. If desired, a suitable high temperature or thermal setting glue may be used to secure the adapter members to the instrument jaws. Alternatively, the adapter members may be welded or soldered to the instrument jaws as at 155. One or more rivits may also be used to secure each adapter member to the instrument jaw as described in detail hereinafter.

The forward portion of the adapter member 104 is provided with a channel 136 which is wider than the channel 36 of the instrument jaw 34. The channel 136 also has a partially cylindrical recess 138 extending across the channel between the walls 150 and 151. In the embodiment illustrated, the recess 138 may be formed by drilling through the walls 150 and 151 thereby forming bores 153 and 154 in the walls 150 and 151, respectively. If the adapter member 104 is fabricated from metal, such as stainless steel, the cylindrical recess 138 is most conveniently formed by means of drilling whereby the bores 153 and 154 are necessarily formed in the adapter member walls 150 and 151, respectively. However, the adapter member 104 may be fabricated from a suitable thermoplastic polymer. In such a case, the partially cylindrical recess 138 may be directly molded into the structure and the bores 153 and 154 need not be drilled or otherwise formed.

The channel 136 of the adapter member 104 is substantially wider than the channel 36 of the instrument jaw 34. This will permit the adapter member 104 to receive the wider clip 10B described above with reference to FIG. 9. Also, the portion of the channel 136 forward of the recess 138 is deeper than the portion of the channel behind recess 138. In this respect, the channel 136 of the adapter member 104 is similar to the channel 36 in the lower jaw 34 of the instrument 30 so as to properly accommodate the clip 10B as it is latched closed.

The upper adapter member 105 of the adapter assembly 100 (FIG. 13) has a structure identical to that of the adapter member 104 described above. Consequently, when the clip 10B is properly positioned with the clip bosses received in the recesses of the adapter members, the clip 10B may be applied to a blood vessel or other duct in a manner identical to that described above for the clip 10A with references to FIGS. 5, 6, and 7.

FIG. 15 illustrates a second embodiment of an adapter assembly for the instrument 30. The second embodiment of the adapter assembly is next described with reference to a first or lower adapter member 204 secured to the lower jaw 34 of the instrument 30 as illustrated in FIG. 15. The second embodiment of the adapter assembly also has a second or upper adapter member (not illustrated) associated with the upper jaw of the instrument 30. The second embodiment of the adapter assembly is designed for use with the clip 10C described above with reference to FIG. 10 and which is generally similar to the clip 10A illustrated in FIGS. 5, 6, and 8 but which has a greater length.

The adapter member 204 has a channel 236 that is similar in configuration to the channel 36 of the lower jaw 34 of the instrument 30 except that the channel 236 is longer than the channel 36. The channel 236 has a recess 238 for receiving the boss of the clip 10C. The adapter member 204 has walls 250 and 251 which engage and receive the instrument lower jaw 34. The adapter member 204 is secured to the instrument lower jaw 34 by suitable means, such as by a weld 255.

The upper adapter member of the second embodiment of the adapter assembly is identical to the lower adapter member 204 illustrated in FIG. 15. The upper and lower adapter members cooperate to receive and to apply the clip 10C in the manner generally analogous to that described above for the clip 10A with reference to FIGS. 5, 6, and 7.

FIG. 16 illustrates a third embodiment of the adapter assembly of the present invention. The third embodiment of the adapter assembly is illustrated and described with reference to a lower jaw adapter member 304 which is identical to an upper jaw adapter member not illustrated. The third embodiment of the adapter assembly is designed for applying the clip 10D described above and designated by the reference numeral 10D in FIG. 11.

The lower jaw adapter member 304 includes a pair of spaced-apart parallel sidewalls 350 and 351 which cooperate together to receive and engage the lower jaw 34 of the instrument. The lower jaw adapter member 304 is mounted to the instrument lower jaw 34 by suitable means, such as glue, adhesive, or a weld 355.

The lower jaw adapter member 304 includes a centrally disposed upstanding guide rail 386 which is adapted to be received in the slot of one of the leg segments of the clip 10D (FIG. 11). The rail 386 aligns the clip 10D on the instrument 30 and a friction fit keeps the clip 10D in the instrument jaws until the clip is closed about a vessel.

To insure that the front end of the clip 10D can be properly latched, the adapter member 304 is provided with a downwardly slanting surface 388 to provide appropriate clearance.

Though not illustrated, upstanding sidewalls may be provided on the lower adapter member 304 on either side of, spaced from, and parallel to, the rail 386. Such additional sidewalls would extend forwardly from the existing instrument jaw walls 50 and 51 to form, in effect, a continuation of the walls 50 and 51.

The third embodiment of the adapter assembly has an upper jaw adapter member (not illustrated in FIG. 16) which is identical to the lower jaw adapter member 304 and which cooperates with the lower jaw adapter member 304 to receive, hold, and apply the clip 10D when the instrument 30 is actuated to close the instrument jaws.

A fourth embodiment of the adapter assembly of the present invention is illustrated in FIG. 17 with reference to a lower jaw adapter member 404. The assembly also has an upper jaw adapter member identical to the lower jaw adapter member 404 (not illustrated in FIG. 17).

Specifically, the lower adapter member 404 has a pair of spaced-apart parallel walls 450 and 451 which engage and receive the front end of the instrument lower jaw 34. The lower adapter member 404 is secured to the lower jaw 34 by suitable means, such as by adhesive or by means of a suitable weld 455.

The lower jaw adapter member 404 includes a clip applying portion having a configuration adapted to engage the clip illustrated in FIG. 12 and designated generally therein by the reference numeral 10E. In particular, the lower jaw adapter member 404 includes a channel of 436 for receiving one leg segment of the clip 10E. Projecting upwardly from the channel 436 is a generally cylindrical boss 489 which is adapted to be received in one of the cylindrical bores or recesses of one of the leg segments of the clip 10E.

The upper jaw adapter member (not illustrated) has a structure identical to that described above for the lower jaw adapter member 404. The two adapter members are designed to cooperate to receive, hold, and apply the clip 10E.

Figure 18:
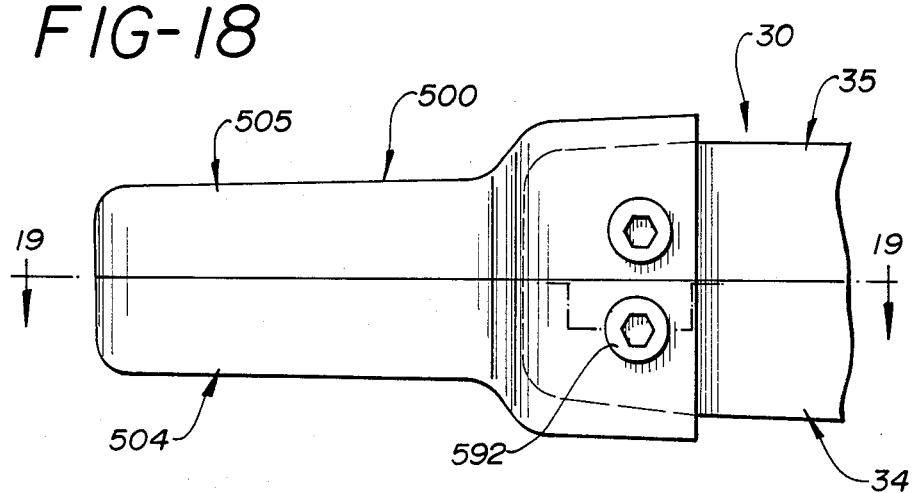
FIG. 18 is a greatly enlarged, side view of the instrument of FIG. 1 shown in a closed position with a fifth embodiment of the adapter assembly of the present invention mounted thereon.
Figure 19:
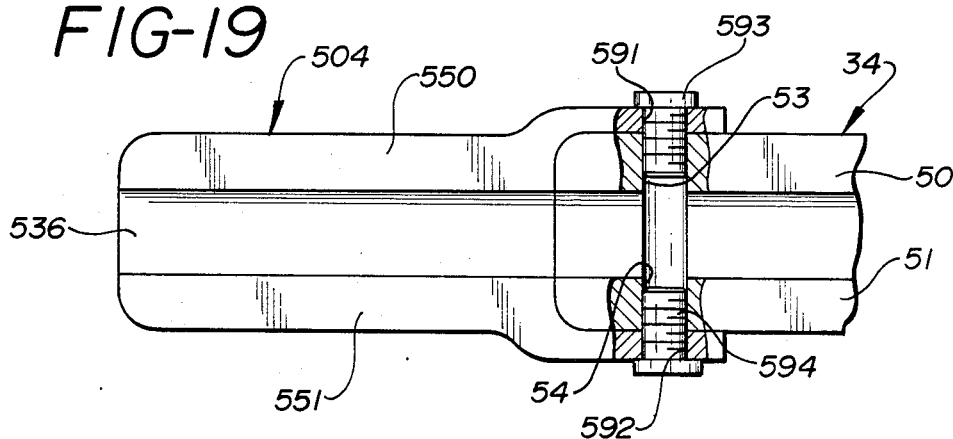
FIG. 19 is a cross-sectional view taken generally along the planes 19—19 in FIG. 18.

FIGS. 18 and 19 illustrate a fifth embodiment of the novel adapter assembly designated generally by the reference numeral 500. The adapter assembly 500 includes an upper jaw adapter member 505 and a lower jaw adapter member 504. The adapter assembly 500 is disclosed to illustrate the novel means by which an adapter assembly may be secured to the jaws 34 and 35 of the clip applier instrument 30. However, the novel attachment means may be used with any of the adapter assemblies described above with reference to FIGS. 13–17.

For purposes of illustration, the clip receiving portions of the adapter assembly 500 have been simplified as best viewed in FIG. 19 for the lower jaw adapter member 504. Specifically, the lower jaw adapter member 504 has a pair of spaced-apart widewalls 550 and 551 between which is defined a clip receiving channel 536. Depending upon the particular configuration of the clip to be applied, the lower jaw adapter member 504 would have a mating clip applying portion with a configuration adapted to cooperate with the other adapter member to receive, hold, and apply the particular clip. For example, the front portion of the adapter member 504 may have a configuration substantially identical to the front portions of any of the lower jaw adapter members described above with reference to FIGS. 14–17.

Regardless of the particular configuration of the clip applying front portion of the adapter member 504, a novel structure is provided for attaching the adapter member 504 to the lower jaw 34 of the instrument 30. Specifically, with continued reference to FIGS. 18 and 19, the lower jaw adapter member 504 extends rearwardly to receive and engage the front portion of the instrument lower jaw 34. Each sidewall 550 and 551 is provided with a bore, namely, bore 591, in sidewall 550 and bore 592 in sidewall 551. The bores 591 and 592 are in registry with the bores 54 and 53 in the instrument lower jaw 34. The bores 53 and 54 of the lower jaw 34 are threaded and adapted to receive screws 593 and 594, respectively. The bores 591 and 592 of the adapter member walls 550 and 551, respectively, are large enough to permit the passage of the screws 593 and 594, respectively.

The upper jaw adapter member 505 of the adapter assembly 500 is similarly secured to the upper jaw 35 of the instrument 30. The upper jaw adapter member 505 has a configuration identical to that of the lower jaw adapter member 504. The two adapter members 504 and 505 thus can cooperate to receive, hold, and apply a clip to a blood vessel or other conduit when the instrument 30 is operated in the usual manner described above.

The above-described jaw adapter member attachment structure avoids the use of adhesive or welds. This has the advantage of permitting the adapter assembly 500 to be easily removed from the instrument if desired. Adapter assemblies for other types of clips could be similarly secured to the instrument if desired.

Figure 20:
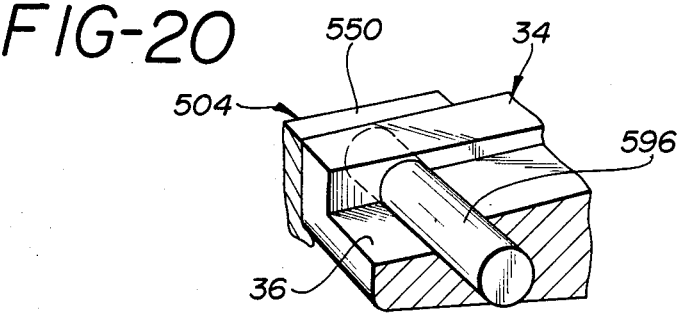
FIG. 20 is an enlarged, fragmentary, perspective view of the front of the lower jaw of the instrument of FIG. 1 with some of the structure cut away and shows a modification of the means for mounting the adapter assembly of FIGS. 18 and 19 to the instrument.

FIG. 20 illustrates a modification of the means for attaching the adapter members to the instrument 30. The modification is illustrated specifically with reference to the lower jaw adapter member 504 secured to the instrument lower jaw 34. Specifically, the screws 593 and 592 of the structure illustrated in FIGS. 18 and 19 are replaced with a single rivit 596. The rivit is received through the instrument jaw bores and engages the rearwardly extending portions of the sidewalls 550 and 551 of the lower jaw adapter member 504.

Figure 21:
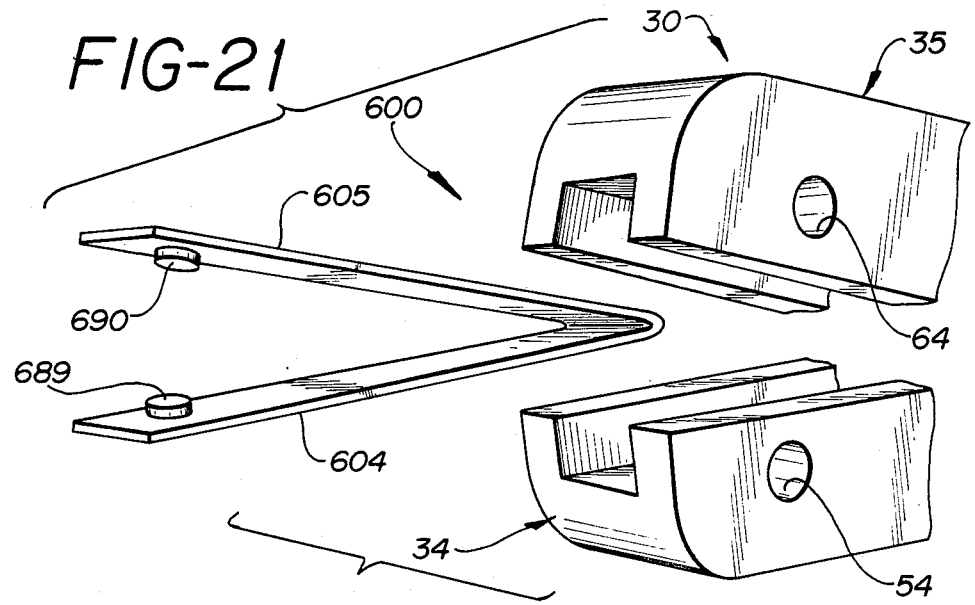
FIG. 21 is an exploded, fragmentary, perspective view of the front portion of the instrument of FIG. 1 and shows a sixth embodiment of the adapter assembly of the present invention.
Figure 22:
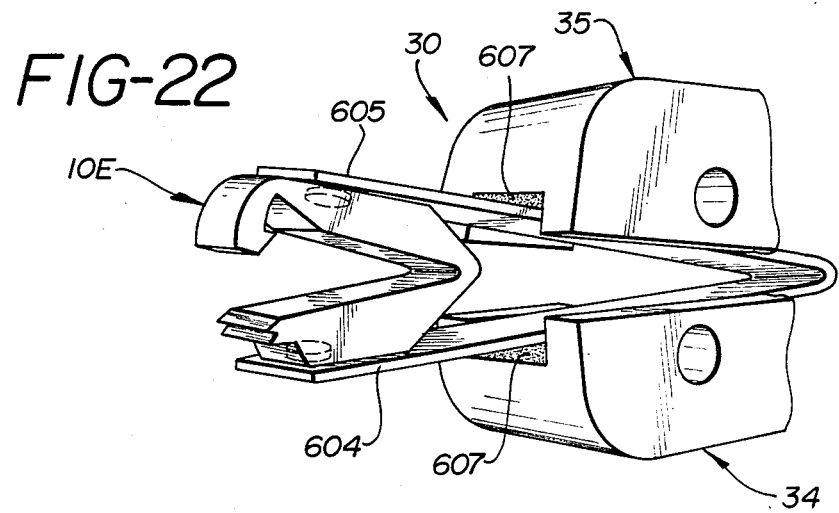
FIG. 22 is a fragmentary, perspective view of the sixth embodiment of the adapter assembly of the present invention shown mounted within the instrument of FIG. 1 and in an open position with a clip of the type illustrated in FIG. 12 disposed within the adapter assembly.
Figure 23:
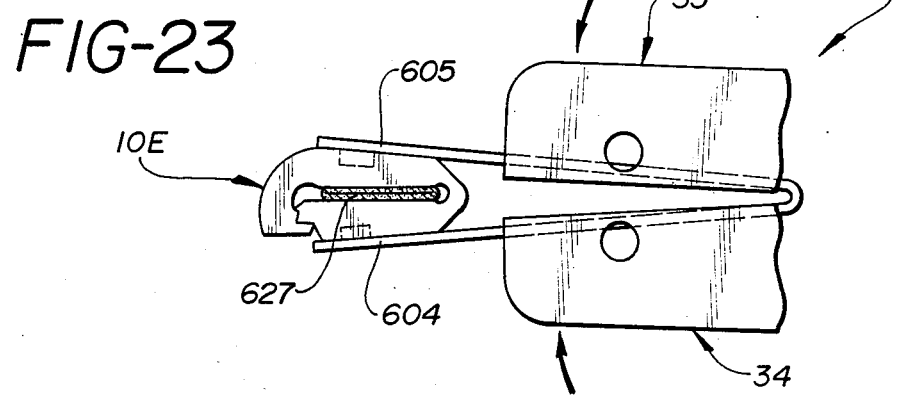
FIG. 23 is a fragmentary, side elevational view of the adapter assembly illustrated in FIG. 22 with the adapter assembly shown in a closed position to close the clip about a blood vessel.

FIGS. 21-23 illustrate a sixth embodiment of the adapter assembly of the present invention which is designated generally in those Figures by the reference numeral 600. The adapter assembly 600 is a unitary assembly that preferably comprises a V-shaped piece of spring steel. The assembly has a first or lower jaw adapter member 604 and a second or upper jaw adapter member 605. The adapter assembly 600 is designed to be inserted within the channels of the instrument lower and upper jaws 34 and 35 as illustrated in FIG. 22. Preferably, the assembly 600 is secured to at least one of the two jaws by appropriate means, such as by glue, by adhesive, by welding, or the like. A suitable glue 607 is shown in the illustrated embodiment in FIG. 22 for securing the assembly 600 to the jaws. Although the glue 607 is shown as applied to both jaws of the instrument 30, the glue may be applied to only one of the jaws.

In the embodiment of the adapter assembly 600 illustrated in FIGS. 21-23, the assembly 600 is designed to be used to apply a clip of the type illustrated in FIG. 12 and generally designated in FIG. 12 by the reference numeral 10E. To this end, the lower jaw adapter member 605 has an upstanding cylindrical boss 689 and the upper jaw adapter member 605 has a downwardly extending cylindrical boss 690 (FIG. 21). The bosses are adapted to be received in the cylindrical apertures of the clip 10E.

The clip 10E is positioned in the assembly 600 as illustrated in FIG. 22 when the instrument 30 is in the open position. Proper actuation of the instrument 30 to close the jaws causes the adapter members 604 and 605 to move toward each other and to thereby latch closed the clip 10E about a vessel or conduit 627 as best illustrated in FIG. 23.

FIGS. 13-23 illustrate a number of embodiments of the adapter assembly of the present invention. Each embodiment is illustrated as having clip applying portions with a particular configuration adapted to receive, hold, and apply a particular type of clip. It is to be realized that the novel adapter assembly of the present invention can include other configurations for the clip applying portions, such other configurations having the shapes and arrangements necessary to engage, receive, hold, and apply the particular clips.

Although the instrument 30 has been illustrated as having bores 64 and 63 in the upper jaw 35 and bores 54 and 53 in the lower jaw 34, it is to be realized that the novel adapter assembly of the present invention may be provided for an instrument that is substantially similar to the instrument 30 illustrated in FIGS. 1-3 but that does not have the bores 63, 64, 53 and 54. In such a case, the adapter assembly could be secured with adhesive or by welding as described above with reference to FIGS. 14-17.

In addition, bores could be drilled into the instrument jaws to permit use of the novel, removable connection structures described above with reference to FIGS. 18-20.

From the foregoing, it will be observed that numerous variations and modifications may be effected without departing from the true spirit and scope of the novel concept of the invention. It is to be understood that no limitation with respect to the specific apparatus and method illustrated herein is intended or should be inferred. It is, of course, intended to cover by the appended claims all such modifications as fall within the scope of the claims.

What is claimed is:

1. In a medical instrument for applying a first type of ligating clip wherein said first type of clip has an extension configuration adapted to be engaged by said instrument and wherein said instrument includes two pivotally connected actuating members, each having on one end a handle and on the other end a jaw for receiving, holding, and applying said first type of clip, each of said jaws defining a channel disposed in confronting relationship with the channel of the other jaw and extending rearwardly from the tip of the jaw, each said jaw including a side wall defining each side wall of the jaw channel, each jaw having a partially cylindrical recess extending across the width of the jaw channel to each jaw side wall, a bore defined through each said jaw side wall in registry with said partially cylindrical recess, the improvement comprising:

an adapter assembly provided with a first and second adapter member associated with each said jaw, respectively, to accommodate a second type of ligating clip having an extension configuration different than that of said first type of clip;

said first member being releasably secured to the channel in one of said jaws and said second member being releasably secured to the channel in the other of said jaws; each said adapter member being inserted in one of said channels; and each adapter member including a clip applying means disposed on the portion of the adapter member extending beyond the tip of each jaw member, said applying means being in facing relationship and adapted to receive, hold and apply said second type of clip.

2. The improvement in accordance with claim 1 further characterized in that said first and second adapter members of the adapter assembly are joined in a V-shape configuration with the joined portion of the V adjacent the cylindrical recesses.

3. The improvement in accordance with claim 2 wherein the adapter assembly is spring steel.

* * * * *